(12) United States Patent
Bouzbouz et al.

(10) Patent No.: US 9,682,929 B2
(45) Date of Patent: Jun. 20, 2017

(54) METALLOPROTEASE INHIBITORS, METHODS FOR PRODUCING SAME, AND THERAPEUTICS USES THEREOF

(71) Applicants: Centre National de la Recherche Scientifique-CNRS, Paris Cedex (FR); Universite de Reims Champagne-Ardenne, Reims Cedex (FR)

(72) Inventors: Samir Bouzbouz, Saint Etienne du Rouvray (FR); Xavier Pannecoucke, Maromme (FR); Azzaq Belaaouaj, Muizon (FR); Laurette Malleret, Reims (FR); Clement Denhez, Reims (FR); Dominique Guillaume, Ville en Selve (FR)

(73) Assignees: CENTRE NATIONAL DE LA RECHERCHE SCIENTIFIQUE—CNRS, Paris (FR); UNIVERSITE DE REIMS CHAMPAGNE-ARDENNE, Reims (FR)

( * ) Notice: Subject to any disclaimer, the term of this patent is extended or adjusted under 35 U.S.C. 154(b) by 0 days.

(21) Appl. No.: 14/915,807

(22) PCT Filed: Sep. 2, 2014

(86) PCT No.: PCT/FR2014/052163
§ 371 (c)(1),
(2) Date: Mar. 1, 2016

(87) PCT Pub. No.: WO2015/028766
PCT Pub. Date: Mar. 5, 2015

(65) Prior Publication Data
US 2016/0200676 A1    Jul. 14, 2016

(30) Foreign Application Priority Data

Sep. 2, 2013  (FR) ...................................... 13 58368

(51) Int. Cl.

| | |
|---|---|
| C07C 237/22 | (2006.01) |
| C07C 319/12 | (2006.01) |
| C07D 231/22 | (2006.01) |
| C07C 231/10 | (2006.01) |
| C07C 235/34 | (2006.01) |
| C07C 231/12 | (2006.01) |
| C07C 69/533 | (2006.01) |
| C07C 67/31 | (2006.01) |
| C07C 323/57 | (2006.01) |
| C07C 235/28 | (2006.01) |
| C07C 323/60 | (2006.01) |
| C07C 67/14 | (2006.01) |
| C07C 69/732 | (2006.01) |
| C07C 323/59 | (2006.01) |
| C07C 67/343 | (2006.01) |

(52) U.S. Cl.
CPC ............ *C07C 319/12* (2013.01); *C07C 67/14* (2013.01); *C07C 67/31* (2013.01); *C07C 67/343* (2013.01); *C07C 69/533* (2013.01); *C07C 69/732* (2013.01); *C07C 231/10* (2013.01); *C07C 231/12* (2013.01); *C07C 235/28* (2013.01); *C07C 235/34* (2013.01); *C07C 237/22* (2013.01); *C07C 323/57* (2013.01); *C07C 323/59* (2013.01); *C07C 323/60* (2013.01); *C07D 231/22* (2013.01); *C07C 2101/14* (2013.01)

(58) Field of Classification Search
None
See application file for complete search history.

(56) References Cited

PUBLICATIONS

Database CAPLUS in STN, Acc. No. 2011:1287448, Bouzbouz, Synlett (2011), 13, pp. 1888-1894 (abstract).*

* cited by examiner

*Primary Examiner* — Brian J Davis
(74) *Attorney, Agent, or Firm* — McAndrews, Held & Malloy, Ltd.

(57) ABSTRACT

The invention relates to new α-vinyl carbonylated compounds corresponding to general formula (I), wherein $R_1$, $R_2$, $R_3$, $R_4$, $R_5$ and Y are as defined in claim 1, their isomers, their diastereoisomers and acid addition salts or a pharmaceutically acceptable base. The invention also relates to a method for producing said compounds (I). It further relates to the use of said compound (I) as selective metalloprotease inhibitors, especially matrix metalloproteases 12 (MMP-12) and/or 9 (MMP-9). The compounds (I) are particularly useful for the prevention and/or treatment of chronic obstructive pulmonary disease (COPD), particularly emphysema induced by cigarette smoke.

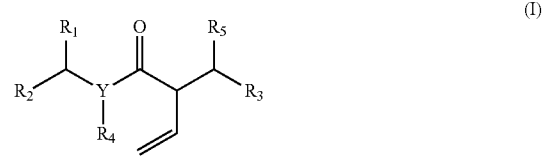

16 Claims, 3 Drawing Sheets

METALLOPROTEASE INHIBITORS, METHODS FOR PRODUCING SAME, AND THERAPEUTICS USES THEREOF

The present application is filed pursuant to 35 U.S.C. 371 as a U.S. National Phase application of International Patent Application No. PCT/FR2014/052163, which was filed Sep. 2, 2014, claiming the benefit of priority to French Patent Application No. 1358368, which was filed on Sep. 2, 2013. The entire text of the aforementioned applications is incorporated herein by reference in its entirety.

The present invention relates to novel selective inhibitors of metalloproteases, and in particular of matrix metalloproteases 12 (MMP-12) and/or 9 (MMP-9). It also relates to the processes for producing said inhibitors and to the therapeutic uses thereof, in particular for preventing and/or treating chronic obstructive pulmonary disease (COPD), in particular emphysema caused by cigarette smoke.

Matrix metalloproteases (MMPs) are proteolytic enzymes characterized by the presence of a $Zn^{2+}$ ion linked to 3 histidine residues, at their catalytic site. These enzymes have roles in extracellular matrix modification. The overexpression of some of these enzymes is involved in many pathological and physiological processes: normal and pathological angiogenesis, embryonic development, healing, connective and joint tissue degeneration, and invasive and metastatic cancers.

Zinc metalloproteases comprise at least thirty members; those of which the substrates are known are: collagenases (interstitial MMP-1, neutrophilic MMP-8 and collagenase-3 or MMP-13), gelatinases A and B (collagenases MMP-2 and MMP-9), metalloelastase MMP-12, stromelysins (including stromelysin-1 or MMP-3) and gelatinase A activators (MT-MMP, only MMP having a transmembrane domain).

Several MMPs are expressed by endothelial cells. Some MMPs increase the release of angiogenic factors, such as VEGF, and play an important role in tumor progression (1). To reversibly block the proteolytic activity of MMPs, it is possible to use synthetic inhibitors which interact directly with the catalytic site of MMPs. These inhibitors will then be therapeutic tools capable of eradicating the progression of pathological conditions.

MMP-9 is an essential enzyme in many physiological processes, such as inflammation or prostate cancer. This MMP also plays a role in the regulation of arterial pressure by certain angiotensin-converting enzymes and with endothelin, but also in the degradation of the cartilaginous matrix with aggrecanase (ADAMTS-4 and 5). Its role has been demonstrated in the regulation of coagulation with carboxypeptidase U.

The involvement of MMP-12 in chronic obstructive pulmonary disease (COPD) has at the current time been confirmed: it has in fact been demonstrated that this enzyme plays an important role in the generation of pulmonary emphysema due to inhalation of tobacco smoke in mice. The role of MMP-12 has more particularly been demonstrated by knocking out the gene encoding this enzyme in mice exposed to tobacco smoke for 6 months. These mice develop neither macrophage alveolitis nor pulmonary emphysema, contrary to the control mice (2).

Chronic obstructive pulmonary disease (COPD) represents a major public health problem throughout the world. In Europe, 4 to 10% of the population suffers from COPD, leading to very significant financial health costs (55 billion euros per year and 28.5 billion euros associated with a loss of productivity in the workplace). Emphysema caused by cigarette smoke, also called pulmonary emphysema, is a physiopathological condition which represents the principal component of COPD. Emphysema is characterized by a distension of the air spaces and a destruction of their wall. Exposure to tobacco smoke is the principal etiological factor in COPD.

Despite the increasing understanding of the physiopathology of COPD, the ways of treating COPD are not yet very developed and are based solely on a symptomatological approach which consists of a pharmacological treatment to which other methods of reducing the symptoms of COPD are added.

The current treatment involves the use of MMP inhibitors which are, for example, anti-inflammatory antibiotics of the macrolide or tetracycline family initially used for treating pulmonary infections. Roxithromycin has been described for reducing MMP-9 expression in neutrophil polymorphonuclear cells, macrophages and nasal epithelial cells ((3), (4)). Doxycycline can also inhibit MMP synthesis and/or activity (5).

MMP inhibitors of another type comprise peptide inhibitors. These compounds have a pseudopeptide structure which mimics the substrate cleavage site. In competition with this substrate, they bind to the catalytic site by chelation of the zinc atom of the enzyme via their hydroxamate or acid hydrophilic functionality ((6), (7)).

Among the inhibitors studied, the most well known are Batimastat and Marimastat (British Biotech). These two molecules are relatively nonselective. A certain number of these peptides have been tested in animals developing emphysema caused by cigarette smoke with promising data. Unfortunately, they have proved to be ineffective during clinical trials, with side effects at the level of the musculoskeletal system (8). The same effects have been observed with other inhibitors (RS-113.456 and CP 471.474) ((9), (10)).

A third class of inhibitors of nonpeptide type has subsequently been developed in order to overcome the lack of selectivity and the low bioavailability of the (pseudo) peptide inhibitors. The most significant molecules in this category are Prinomastat (AG3340) (Agouron-Pfizer), BAY 12-9566 (Bayer), BMS-275291 (Bristol-Myers Squibb) and CGS-27023 (Novartis) ((11), (12)).

Despite the selected spectrum of inhibition of these molecules, their significance has been ruined by varied side effects (musculoskeletal toxicity, skin toxicity, hepatic toxicity and induction of thromobocytopenia) ((13), (14)).

Thus, despite certain advances in animals, the human studies have not been satisfactory and there is, at the current time, no metalloprotease inhibitor approved for use in humans suffering from COPD.

There therefore remains at the current time a need to design and synthesize novel selective metalloprotease inhibitors.

One of the objectives of the present invention is therefore to design novel selective inhibitors of metalloproteases, and in particular of matrix metalloproteases 12 (MMP-12) and/or 9 (MMP-9).

Another objective of the invention is to design novel compounds which are active against chronic obstructive pulmonary disease (COPD), and in particular against emphysema caused by cigarette smoke.

Another objective of the invention is to design a process for producing said selective MMP-inhibitor active compounds, which is at the same time rapid (limited number of steps), easy to carry out, inexpensive and reproducible on an industrial scale.

A subject of the present invention is thus an α-vinyl carbonyl compound characterized in that it has formula (I):

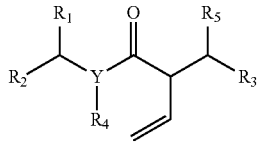

(I)

in which $R_1$ represents an acyl radical of formula —CO—$R_8$, in which $R_8$ represents OH, $NHR_{10}$ or $NR_{10}R_{11}$, with $R_{10}$ and $R_{11}$, which may be identical or different, representing, independently of one another, hydrogen, alkyl, alkenyl, alkynyl, OH, phenyl ($C_6H_5$), methoxyphenyl ($C_6H_4OCH_3$), phenyloxyphenyl ($C_6H_4OC_6H_5$), biphenyl ($C_{12}H_9$), benzyl ($CH_2C_6H_5$), cyclohexyl ($C_6H_{11}$) or cyclopentyl ($C_5H_9$), $R_2$ or $R_3$, which may be identical or different, represent, independently of one another:

an alkyl, alkenyl or alkynyl radical, a —$(CH_2)_n$—$R_{12}$ radical, in which n represents an integer ranging from 1 to 6, with $R_{12}$ representing OH, phenyl, biphenyl, benzyl, cyclohexyl, cyclopentyl, COOH, $COOR_9$, $SR_9$ or $S^-$ (cation), with $R_9$ representing hydrogen, alkyl, alkenyl or alkynyl, a —$(CH_2)_n$—N—$(R_9)_2$ or —$(CH_2)_n$—N—$(COO—R_9)_2$ radical, a cycloalkyl radical, preferably chosen from cyclopropyl, cyclobutyl, cyclopentyl, cyclohexyl or 2-isopropyl-5-methylcyclohexyl, an aryl radical, preferably chosen from phenyl ($C_6H_5$), methoxyphenyl ($C_6H_4OCH_3$), phenyloxyphenyl ($C_6H_4OC_6H_5$), benzyl ($C_6H_5CH_2$), phenethyl ($C_6H_5CH_2CH_2$), tolyl ($C_6H_4CH_3$), xylyl ($C_6H_3(CH_3)_2$), benzylidene ($C_6H_5CH$), benzoyl ($C_6H_5CO$), biphenyl (or diphenyl) ($C_{12}H_9$), naphthyl ($C_{10}H_7$), pyrazole or 5-(4-methoxybenzyloxy)-1-phenylpyrazole, it being possible for $R_1$ and $R_2$ to also together form a cycloalkyl or aryl radical, Y represents a nitrogen or oxygen atom, $R_4$ represents a hydrogen atom, an alkyl, alkenyl, alkynyl or aryl radical, a doublet of electrons, a —$(CH_2)_n$—$R_{12}$ radical with n and $R_{12}$ as previously defined, $R_5$ represents:

an $XR_6R_7$ radical with X representing an oxygen, nitrogen or sulfur atom, $R_6$ and $R_7$, which may be identical or different, representing, independently of one another, a hydrogen atom, an alkyl radical, a doublet of electrons, an $SO_2R_{13}$ radical with $R_{13}$ representing an alkyl, alkenyl, alkynyl, aryl radical as previously defined, a —$(CH_2)_n$—$R_{12}$ radical as previously defined, a halogen, an alkyl, alkenyl, alkynyl radical, isomers thereof, diastereoisomers thereof and addition salts thereof with a pharmaceutically acceptable acid or base.

In the present application, the term "alkyl" denotes a linear or branched hydrocarbon-based radical advantageously having from 1 to 12 carbon atoms, and preferably from 1 to 6 carbon atoms, such as methyl, ethyl, propyl, isopropyl, butyl, tert-butyl, pentyl, neopentyl or n-hexyl.

The term "alkenyl" denotes a linear or branched hydrocarbon-based radical comprising one or more carbon-carbon double bonds, advantageously having from 2 to 12 carbon atoms, and preferably from 2 to 6 carbon atoms, with one or two double bonds.

The term "alkynyl" denotes a linear or branched hydrocarbon-based radical comprising one or more carbon-carbon triple bonds, advantageously having from 2 to 12 carbon atoms, and preferably from 2 to 6 carbon atoms, with one or two triple bonds.

The term "cyclohexyl" denotes a cyclic hydrocarbon-based system which can advantageously comprise from 3 to 8 carbon atoms, preferably from 3 to 6, and be monocyclic or polycyclic.

The term "aryl" denotes a monocyclic, bicyclic or tricyclic aromatic hydrocarbon-based system having from 6 to 18 carbon atoms, and which can be substituted or unsubstituted.

The alkyls, alkenyls, alkynyls and cycloalkyls as defined above can also be substituted.

The term "halogen" denotes fluorine, chlorine, bromine or iodine.

Regarding the substituents $R_{13}$, $R_{10}$, $R_{11}$, $R_2$ or $R_3$, when they represent for example a methoxyphenyl ($C_6H_4OCH_3$), then the methoxy group can be substituted in the ortho-, meta- or para-position with respect to the phenyl. The same is true for phenyloxyphenyl ($C_6H_4OC_6H_5$) for which the $OC_6H_5$ group can be substituted in the ortho-, meta- or para-position with respect to the phenyl.

Regarding the substituent $R_{12}$ and the designation "$S^-$ (Cation)", "$S^-$" denotes a negatively charged sulfur and "Cation" denotes a positively charged cation, it being possible for said cation to denote an organic or metal cation. By way of example of an organic cation, mention may be made of an ammonium, trialkylammonium or pyridinium cation. By way of example of a metal cation, mention may be made of a sodium cation ($Na^+$), lithium cation ($Li^+$) or potassium cation ($K^+$).

According to one embodiment of the invention, the compounds of the invention are more particularly represented by formula (I) below:

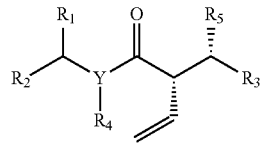

in which $R_1$, $R_2$, $R_4$, $R_5$, $R_3$ and Y are as previously defined.

According to one advantageous embodiment of the invention, in the compound of formula (I):

Y represents a nitrogen atom and $R_4$ represents a hydrogen atom, $R_5$ represents an $XR_6R_7$ radical in which X represents an oxygen atom, $R_6$ represents a hydrogen and $R_7$ represents a doublet of electrons, $R_1$ represents an acyl radical —CO—$R_8$, in which $R_8$ represents OH or $NHR_{10}$ with $R_{10}$ as previously defined, $R_2$ represents a —$(CH_2)_n$—$R_{12}$ radical, a —$(CH_2)_n$—N—$(R_9)_2$ radical or an aryl radical as previously defined, $R_3$ represents an alkyl or aryl radical as previously defined.

By way of examples of particularly advantageous compounds of formula (I) of the invention, mention may be made of one of those chosen from the group comprising:

- (S)—N—((S)-1-(cyclohexylamino)-1-oxo-3-phenylpropan-2-yl)-2-(R)-1-hydroxyethyl)but-3-enamide,
- (S)-2-((S)-biphenyl-4-yl(hydroxyl)methyl)-N—((S)-1-(cyclohexylamino)-1-oxo-3-phenylpropan-2-yl)but-3-enamide,
- (S)—N—((S)-1-(cyclohexylamino)-1-oxo-3-phenylpropan-2-yl)-2-((S)-hydroxy-(5-(4-methoxybenzyloxy)-1-phenyl-1H-pyrazol-3-yl)methyl)but-3-enamide,
- (S)-2-((S)-2-((S)-hydroxy-5(4-methoxybenzyloxy)-1-phenyl-1H-pyrazol-3-yl)methyl)but-3-enamido)-3-phenylpropanoic acid,
- (S)-2-((S)-hydroxy-(5-(4-methoxybenzyloxy)-1-phenyl-1H-pyrazol-3-yl)methyl-N—((S)-1-(hydroxyamino)-1-oxo-3-phenylpropan-2-yl)but-3-enamide,
- (S)-2-((S)-2-((S)-hydroxy-(5-(4-methoxybenzyloxy)-1-phenyl-1H-pyrazol-3-yl)methyl)but-3-enamido)succinic acid,
- (S)-2-((2S,3R)-3-hydroxy-2-vinylheptanamido)-4-(methylthio)butanoic acid,
- (S)-2-((R)-1-hydroxyethyl)-N—((S)-1-oxo-1-(4-phenoxyphenylamino)-3-phenylpropan-2-yl)but-3-enamide,
- (S)-3-((S)-2-((R)-1-hydroxyethyl)but-3-enamido)-4-oxo-4-(4-phenoxy-phenylamino)butanoic acid,
- (S)-2-((R)-1-hydroxyethyl)-N—((R)-3-mercapto-1-oxo-1-(4-phenoxyphenyl-amino)propan-2-yl)but-3-enamide,
- (S)—N—((R)-1-(cyclohexylamino)-3-mercapto-1-oxopropan-2-yl)-2-((R)-1-hydroxyethyl)but-3-enamide, and mixtures thereof.

According to another advantageous embodiment of the invention, in the compound of formula (I):
- Y represents an oxygen atom and $R_4$ represents a doublet of electrons,
- $R_5$ represents an $XR_6R_7$ radical in which X represents an oxygen atom, $R_6$ represents a hydrogen and $R_7$ represents a doublet of electrons,
- $R_1$ and $R_2$ together form a cycloalkyl or aryl radical.

By way of example of a particularly advantageous compound of formula (I) of the invention, mention may be made of (S)-((1S,2R,5S)-2-isopropyl-5-methylcyclohexyl)-2-((R)-1-hydroxyethyl)but-3-enoate.

A subject of the present invention is also a process for producing the compounds of formula (I), in which Y represents a nitrogen atom, said process being characterized in that it comprises the following steps:

reacting a compound of formula (II):

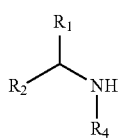

(II)

with $R_1$, $R_2$ and $R_4$ as previously defined, with a compound of formula (II'):

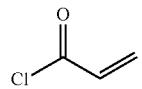

(II')

so as to produce the compounds of formula (III),

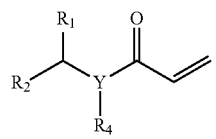

(III)

with $R_1$, $R_2$ and $R_4$ as previously defined, Y representing a nitrogen atom, reacting the compound (III) obtained in the previous step, under neutral conditions, with a compound of formula (III'):

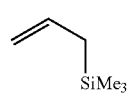

(III')

so as to produce the compounds of formula (IV):

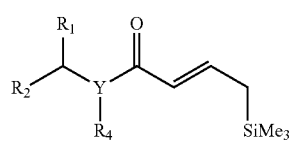

(IV)

with $R_1$, $R_2$, $R_4$ and Y as previously defined, reacting the compound of formula (IV) obtained in the previous step, under basic conditions, with a compound of formula (IV'):

$R_3$CHO  (IV')

with $R_3$ as previously defined, so as to produce the compounds of formula (I):

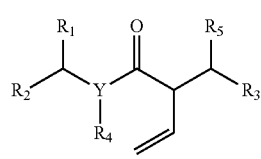

(I)

in which $R_1$, $R_2$, $R_3$ and $R_4$ are as defined in formula (I),
Y represents a nitrogen and $R_5$ represents an $XR_6R_7$ radical in which X represents an oxygen, $R_6$ a hydrogen and $R_7$ a doublet of electrons, namely $R_5$ represents an OH radical.

The step of reacting the compound (II) in the presence of the compound (II') is carried out by means of reaction for substitution, according to conventional organic synthesis conditions, of the primary or secondary amine function with said compound (II').

The invention also relates to a process for producing the compounds of formula (I) as defined above, in which Y represents an oxygen atom, said process being characterized in that it comprises the following steps:

reacting a compound of formula (V):

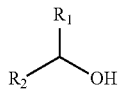
(V)

with $R_1$ and $R_2$ as previously defined, with a compound of formula (II'):

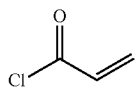
(II')

so as to produce the compounds of formula (VI):

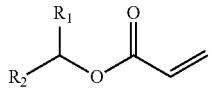
(VI)

with $R_1$ and $R_2$ as previously defined, reacting the compound (VI) obtained in the previous step, under neutral conditions, with a compound of formula (III'):

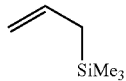
(III')

so as to produce the compounds of formula (VII):

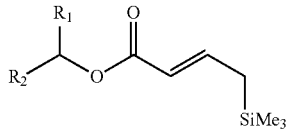
(VII)

with $R_1$ and $R_2$ as previously defined, reacting the compound of formula (VII) obtained in the previous step, under basic conditions, with a compound of formula (IV'):

$R_3CHO$ (IV')

with $R_3$ as previously defined, so as to produce the compounds of formula (I):

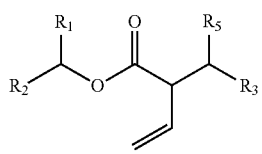
(I)

in which $R_1$, $R_2$ and $R_3$ are as defined in formula (I), $R_5$ represents an $XR_6R_7$ radical in which X represents an oxygen, $R_6$ a hydrogen and $R_7$ a doublet of electrons, namely $R_5$ represents an OH radical.

The step of reacting the compound (V) in the presence of the compound (II') is carried out by means of a reaction for substitution, according to conventional organic synthesis conditions, of the secondary alcohol function with said compound (II').

A subject of the invention is also a compound of formula (I) for its use as a medicament, and more particularly for its use in the prevention and/or treatment of chronic obstructive pulmonary disease (COPD), in particular emphysema caused by cigarette smoke.

According to one particularly advantageous embodiment, the invention relates to a compound of formula (I) for selectively inhibiting at least one metalloprotease chosen from matrix metalloprotease 12 (MMP-12) or 9 (MMP-9).

A subject of the invention is also a composition comprising at least one compound of formula (I) and optionally at least one pharmaceutically acceptable excipient.

More particularly, the invention relates to the composition as defined above, for its use thereof as a medicament.

According to one advantageous embodiment, the invention relates to a composition as defined above, for use thereof in the prevention and/or treatment of chronic obstructive pulmonary disease (COPD), in particular emphysema caused by cigarette smoke.

The form of the pharmaceutical compositions, the route of administration thereof, the dosage thereof and the dosage regimen thereof naturally depend on the severity of the pathological condition, of its stage of progression, on the age, sex and weight of the subject to be treated, etc.

Those skilled in the art will therefore take care to adjust the dosages according to the patient to be treated.

The pharmaceutical compositions according to the invention can be formulated for topical, oral, systemic, parenteral, intravenous, intramuscular, subcutaneous administration, or the like. According to the mode of administration, the composition according to the invention can be in any of the appropriate galenical forms.

The compounds (I) of the present invention are particularly advantageous since they have proven to be metalloprotease inhibitors which do not require chelation due to the presence of the hydroxamic acid function, contrary to most metalloprotease inhibitors, for instance Marimastat and Batimastat.

The compounds of the invention are therefore of use for the treatment of certain cancers, of rheumatic diseases such as arthrosis and rheumatoid arthritis, of Alzheimer's disease and also pulmonary emphysema (principal component of COPD).

A subject of the invention is also the use of a compound of formula (I) for producing a medicament, in particular a medicament intended for the treatment of chronic obstructive pulmonary disease (COPD), and more particularly emphysema caused by cigarette smoke.

Another subject of the invention also relates to methods for treating a subject suffering from COPD, in particular emphysema caused by cigarette smoke, comprising the step of administering, to said subject, a therapeutically effective amount of at least one compound (I) or of a composition of the invention.

The term "therapeutically effective amount" is intended to mean an amount sufficient to treat and/or stop said COPD.

The invention will be understood more clearly on reading the following nonlimiting and purely illustrative examples.

BRIEF DESCRIPTION OF THE DRAWINGS

FIG. 1 illustrates the synthesis scheme for the compounds of formula (I) in which Y represents a nitrogen atom, and FIG. 2 illustrates the synthesis scheme for the compounds of formula (I) in which Y represents an oxygen atom and $R_4$ a doublet of electrons.

EXAMPLE 1

Figure 1:
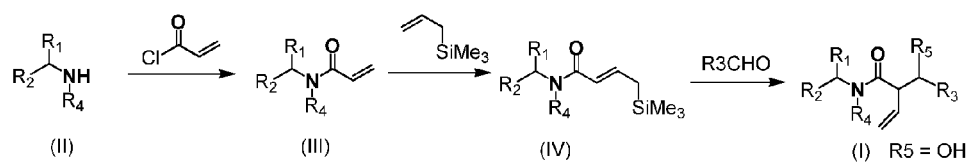
FIGS. 1 and 2 illustrate the synthesis scheme for the compounds of formula (I) of the invention. More particularly.
Figure 2:
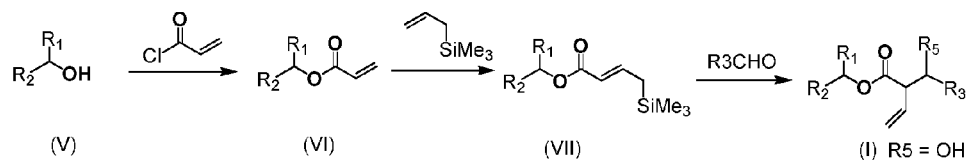

Processes for Producing 7 Compounds Corresponding to General Formula (I) in which Y Represents a Nitrogen Atom The 7 compounds synthesized in this example are hereinafter denoted 1 to 7. They correspond to formula (I) in which:

Y represents a nitrogen and $R_4$ represents a hydrogen atom, $R_5$ represents an $XR_6R_7$ radical in which X represents an oxygen atom, $R_6$ represents a hydrogen atom and $R_7$ represents a doublet of electrons.

Preparation of Compound 1

(S)—N—((S)-1-(cyclohexylamino)-1-oxo-3-phenyl-propan-2-yl)-2-((R)-1-hydroxyethyl)but-3-enamide

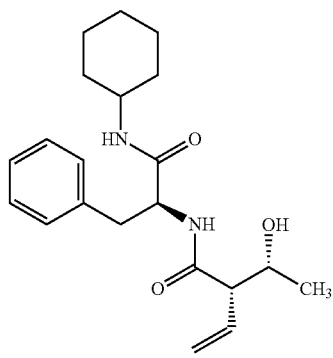

Compound 1 corresponds to formula (I) in which:
$R_1$=acyl radical —$COR_8$ with $R_8$=$NHR_{10}$ with $R_{10}$ representing a cyclohexyl,
$R_2$=—$(CH_2)_n$—$R_{12}$, with n=1 and $R_{12}$=phenyl,
$R_3$=alkyl radical, namely a methyl ($CH_3$).

Stage A

Preparation of (S)—N-(1-cyclohexylamino)-1-oxo-3-phenylpropan-2-yl)acryl-amide 6 mmol (millimol) of triethylamine and then 6 mmol of acryloyl chloride are added, at 0° C., under an inert atmosphere, to a solution of 5 mmol of H-Phe-cyclohexylamide in 20 ml of THF (tetrahydrofuran). After stirring for 1 hour at ambient temperature, the reaction mixture is hydrolyzed with an ammonium chloride solution, and then the mixture is extracted with ethyl acetate (3 times) and with dichloromethane (twice). The organic phases are dried over sodium sulfate, filtered, and concentrated under reduced pressure. Silica gel chromatography (dichloromethane/methanol: 99/1) makes it possible to isolate the expected product in solid form.

Stage B

Preparation of (S,E)-N-(1-cyclohexylamino)-1-oxo-3-phenylpropan-2-yl)-4-(trimethylsilyl)but-2-enamide 6 mmol of allyltrimethylsilane and 0.1 mmol of the catalyst 1,3-bis(2,4,6-trimethylphenyl)-2-imidazolidinylidene)dichloro(o-isopropoxyphenylmethylene)-ruthenium are added to a solution of 2 mmol of the compound obtained in stage A in 15 ml of dichloromethane. After stirring for 24 hours at ambient temperature, the solution is evaporated under vacuum, and silica gel chromatography (dichloromethane/methanol: 99/1) makes it possible to isolate the expected product in solid form.

Stage C

Preparation of (S)—N—((S)-1-(cyclohexylamino)-1-oxo-3-phenylpropan-2-yl)-2-((R)-1-hydroxyethyl)but-3-enamide (1)

1.1 mmol of acetaldehyde and then 1.1 mmol of tetrabutylammonium fluoride are added successively, at −78° C., to a solution of 1 mmol of the compound obtained in stage B in 15 ml of THF or of acetone. After stirring for 15 minutes at this same temperature, the reaction mixture is hydrolyzed with a saturated ammonium chloride solution, and then extracted with ethyl acetate (3 times). The organic phases are dried over sodium sulfate, filtered, and concentrated under reduced pressure. Silica gel chromatography (dichloromethane/methanol: 99/1) makes it possible to isolate the expected product 1 in solid form. HRMS calculated: 381.2154 [(M+Na+), $C_{21}H_{30}N_2O_3Na$]. found: 381.2155, $^1$H NMR (CDCl$_3$, 300 MHz) δ: 7.27-7.14 (m, 5H), 6.73 (d, J=9 Hz, 1H, NH), 5.94-5.74 (m, 1H), 5.71 (d, J=6 Hz, 1H, NH), 5.27 (d, J=14.9 Hz, 1H), 5.18 (d, J=9.8 Hz, 1H), 4.53 (m, 1H), 4.09 (m, 1H), 3.60 (m, 1H), 3.09-2.76 (m, 2H+1H), 1.75-0.88 (m, 10H), 1.08 (d, J=6.7 Hz, 3H).

Preparation of Compound 2

(S)-2-((S)-biphenyl-4-yl(hydroxy)methyl)-N—((S)-1-(cyclohexylamino)-1-oxo-3-phenylpropan-2-yl)but-3-enamide

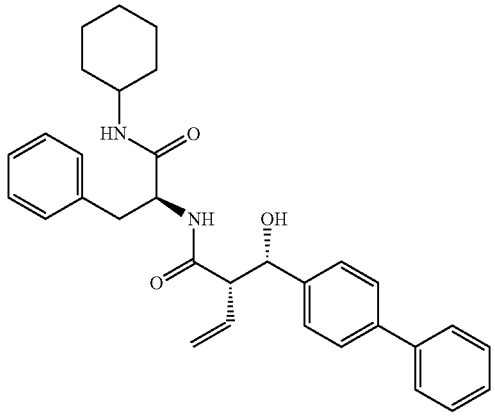

2

Compound 2 corresponds to formula (I) in which:
$R_1$ and $R_2$ have the same meaning as for compound 1,
$R_3$=aryl radical, namely a biphenyl.
Stages A and B: similar to stages A and B for compound 1.

Stage C

Preparation of (S)-2-((S)-biphenyl-4-yl(hydroxyl)methyl)-N—((S)-1-(cyclohexylamino)-1-oxo-3-phenylpropan-2-yl)but-3-enamide (2)

0.5 mmol of 4-biphenylaldehyde and then 0.55 ml of tetrabutylammonium fluoride are added successively, at −78° C., to a solution of 0.5 mmol of the compound obtained in stage B in 15 ml of THF or acetone. After stirring for 15 minutes at this same temperature, the reaction mixture is hydrolyzed with a saturated ammonium chloride solution, and then extracted with ethyl acetate (3 times). The organic phases are dried over sodium sulfate, filtered, and concentrated under reduced pressure. Silica gel chromatography (dichloromethane/methanol: 99/1) makes it possible to isolate the expected product 2 in solid form. HRMS calculated: 497.2804 [(M+$^+$), $C_{32}H_{37}N_2O_3$]. found: 497.2801. $^1$H NMR (DMSO, 300 MHz) δ: 8.31 (d, J=9 Hz, 1H, NH) 7.70-7.14 (m, 5H+9H), 5.81 (d, J=6 Hz, 1H, NH), 5.60-5.45 (m, 1H), 4.80-4.65 (m, 2H+1H), 4.53 (m, 1H), 3.53 (m, 1H), 3.34-3.10 (m, 2H), 2.78 (m, 1H), 1.74-1.04 (m, 10H).

Preparation of Compound 3

(S)—N—((S)-1-(cyclohexylamino)-1-oxo-3-phenyl-propan-2-yl)-2-4S)-hydroxy-(5-(4-methoxybenzyloxy)-1-phenyl-1H-pyrazol-3-yl)methyl)but-3-enamide

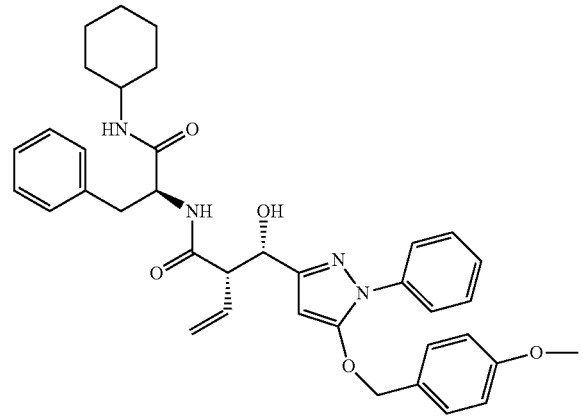

3

Compound 3 corresponds to formula (I) in which:
$R_1$ and $R_2$ have the same meaning as for compound 1,
$R_3$=aryl radical, namely 5-(4-methoxybenzyloxy)-1-phenylpyrazole.
Stages A and B: similar to stages A and B for compound 1.

Stage C

Preparation of (S)—N—((S)-1-(cyclohexylamino)-1-oxo-3-phenylpropan-2-yl)-2-((S)-hydroxy(5-(4-methoxybenzyloxy)-1-phenyl-1H-pyrazol-3-yl)methyl)but-3-enamide (3)

0.5 mmol of 5-(4-methoxybenzyloxy)-1-phenyl-1H-pyrazole-3-carbaldehyde and then 0.55 ml of tetrabutylammonium fluoride are added successively, at −78° C., to a solution of 0.5 mmol of the compound obtained in stage B in 15 ml of THF or acetone. After stirring for 15 minutes at this same temperature, the reaction mixture is hydrolyzed with a saturated ammonium chloride solution, and then extracted with ethyl acetate (3 times). The organic phases are dried over sodium sulfate, filtered, and concentrated under reduced pressure. Silica gel chromatography (dichloromethane/methanol: 99/1) makes it possible to isolate the expected product 3 in solid form. HRMS calculated: 623.3233 [(M+H$^+$), $C_{37}H_{43}N_4O_5$]. found: 623.3220. $^1$H NMR (CDCl$_3$, 300 MHz) δ: 7.66-6.88 (1 m, 14H), 6.13 (d, J=9 Hz, 1H, NH), 5.94 (m, 1H), 5.75 (s, 1H), 5.24 (m, 2H), 5.02 (s, 2H), 4.92 (d, 1H, NH), 4.69-4.57 (m, 2H), 3.81 (s, 3H), 3.77 (m, 1H), 3.49 (m, 1H), 3.13-2.96 (m, 2H+1H), 1.71-0.88 (m, 10H).

Preparation of Compound 4

(S)-2-((S)-2-((S)-hydroxy-(5-(4-methoxybenzyloxy)-1-phenyl-1H-pyrazol-3-yl)methyl)but-3-enamido)-3-phenylpropanoic acid

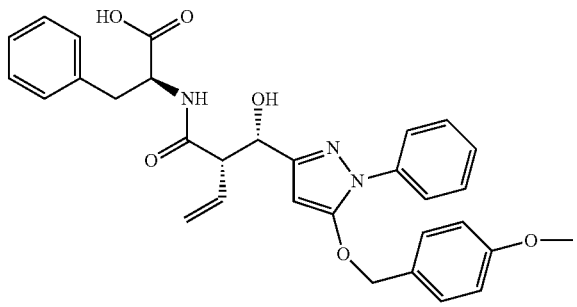

4

Compound 4 corresponds to formula (I) in which:
$R_1$=acyl radical —$COR_8$ with $R_8$=OH,
$R_2$ has the same meaning as for compound 1,
$R_3$ has the same meaning as for compound 3.

Stage A

Preparation of (S)-methyl-2-acrylamido-3-phenylpropanoate 44 mmol of triethylamine and then 20 mmol of acryloyl chloride are added, at 0° C., under an inert atmosphere, to a solution of 20 mmol of H-Phe-alanine methyl ester hydrochloride in 40 ml of THF. After stirring for 1 hour at ambient temperature, the reaction mixture is hydrolyzed, and then extracted with ethyl acetate (3 times) and with dichloromethane (twice). The organic phases are dried over sodium sulfate, filtered, and concentrated under reduced pressure. Silica gel chromatography (cyclohexane/EtOAc: 7/3) makes it possible to isolate the expected product in the form of a white solid.

Stage B

Preparation of (S,E)-methyl 3-phenyl-2-(4-(trimethylsilyl)but-2-enamido)-propanoate 36 mmol of allyltrimethylsilane and 0.2 mmol of the catalyst 1,3-bis(2,4,6-trimethylphenyl)-2-imidazolidinylidene)dichloro(o-isopropoxyphenylmethylene)-ruthenium are added to a solution of 12 mmol of the compound obtained in stage A in 20 ml of dichloromethane. After stirring for 76 hours at ambient temperature, the solution is evaporated under vacuum, and silica gel chromatography (cyclohexane/EtOAc: 7/3) makes it possible to isolate the expected product in the form of a cream solid.

Stage C

Preparation of (S)-methyl 2-((S)-2-((S)-hydroxy-(5-(4-methoxybenzyloxy)-1-phenyl-1H-pyrazol-3-yl)methyl)but-3-enamido)-3-phenylpropanoate 1 mmol of 5-(4-methoxybenzyloxy)-1-phenyl-1H-pyrazole-3-carbaldehyde and then 1.1 ml of tetrabutylammonium fluoride are added successively, at −78° C., to a solution of 1 mmol of the compound obtained in stage B in 15 ml of THF or acetone. After stirring for 15 minutes at this same temperature, the reaction mixture is hydrolyzed with a saturated ammonium chloride solution, and then extracted with ethyl acetate (3 times). The organic phases are dried over sodium sulfate, filtered, and concentrated under reduced pressure. Silica gel chromatography (cyclohexane/EtOAc: 7/3) makes it possible to isolate the expected product in solid form.

Stage D (S)-2-((S)-2-((S)-hydroxy-(5-(4-methoxybenzyloxy)-1-phenyl-1H-pyrazol-3-yl)methyl)but-3-enamido)-3-phenylpropanoic acid (4)

2.4 mmol of LiOH are added to 0.8 mmol of the compound obtained in stage C in a 3/1: THF/$H_2O$ mixture. After stirring for 3 hours at 25° C., the solvents are evaporated off and the residual aqueous phase is diluted with water, acidified to pH=2 by adding a 5% hydrochloric acid solution, and then extracted with ethyl acetate. The combined organic phases are washed, dried, filtered, and then evaporated under reduced pressure. Silica gel chromatography (dichloromethane/methanol: 92/8) makes it possible to isolate the expected product 4 in solid form. HRMS calculated: 540.2135 [(M−H$^+$), $C_{31}H_{30}N_3O_6$]. found: 540.2141. $^1$H NMR (CDCl$_3$, 300 MHz) δ: 7.57-6.87 (1 m, 14H+NH), 6.04 (m, 1H), 5.80 (s, 1H), 5.31-4.97 (m, 2H+NH), 5.02 (s, 2H, OCH2), 4.77 (m, 2H), 3.81 (s, 3H), 3.45-2.94 (m, 2H+1H+OH).

Preparation of Compound 5

(S)-2-((S)-hydroxy-(5-(4-methoxybenzyloxy)-1-phenyl-1H-pyrazol-3-yl)methyl)-N—((S)-1-(hydroxyamino)-1-oxo-3-phenylpropan-2-yl)but-3-enamide

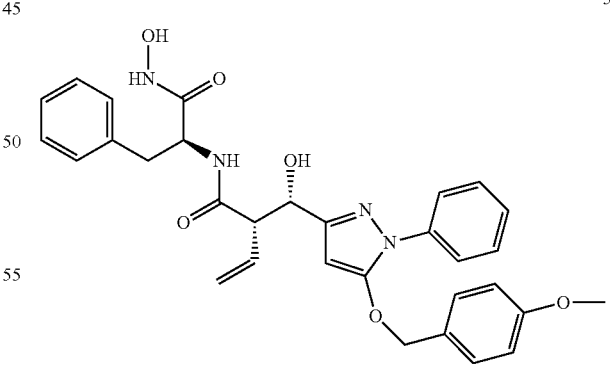

5

Compound 5 corresponds to formula (I) in which:
$R_1$=acyl radical —$COR_8$ with $R_8$=$NHR_{10}$ and $R_{10}$=OH,
$R_2$ has the same meaning as for compound 1,
$R_3$ has the same meaning as for compound 3.
Stages A, B, C, D: similar to stages A, B, C and D for compound 4.

Stage E

Preparation of (S)—N—((S)-1-(tert-butyldimethyl-silyloxyamino)-1-oxo-3-phenylpropan-2-yl)-2-((S)-hydroxy-(5-(4-methoxybenzyloxy)-1-phenyl-1H-pyrazol-3-yl)methyl)but-3-enamide 0.6 mmol of the compound obtained in stage D, 0.6 mmol of 1-hydroxybenzo-triazole, 3 mmol of N-methylmorpholine and 1.2 mmol of 0-silyltertbutyldimethylhydroxylamine hydrochloride are dissolved in 9 ml of dichloromethane. 0.78 mmol of N-[(dimethylamino)propyl]-N-ethylcarbodiimide hydrochloride is then added to this solution and the reaction is stirred at ambient temperature for 12 hours. The reaction mixture is then diluted by adding water, and then extracted with dichloromethane. The combined organic phases are washed with a saturated NaCl solution, dried over sodium sulfate, filtered, and concentrated under reduced pressure. Silica gel chromatography (dichloromethane/methanol: 99/1) makes it possible to isolate the product in the form of a syrup.

Stage F

Preparation of (S)-2-((S)-hydroxy-(5-(4-methoxy-benzyloxy)-1-phenyl-1H-pyrazol-3-yl)methyl)-N—((S)-1-hydroxyamino)-1-oxo-3-phenylpropan-2-yl)but-3-enamide (5)

A solution containing 0.31 mmol of the compound obtained in stage E in 2 ml of THF and 2 ml of TBAF (2 mmol) is stirred for 1 hour at ambient temperature. The reaction mixture is then diluted by adding water, and then extracted with ethyl acetate. The combined organic phases are washed with a saturated NaCl solution, dried over sodium sulfate, filtered, and concentrated under reduced pressure. Silica gel chromatography (dichloromethane/methanol: 99/1) makes it possible to isolate the product 5 in solid form. HRMS calculated: 555.2244 [(M–H$^+$), $C_{31}H_{31}N_4O_6$]. found: 555.2247. $^1$H NMR (CDCl$_3$, 300 MHz) δ: 10.04 (bs, 1H, NH—OH), 7.59-6.64 (1 m, 14H+NH), 5.79-5.59 (m, 1H+1H pyrazole), 5.10-4.76 (1 m, 2H+NH), 4.90 (s, 2H, OCH2), 4.59 (m, 2H), 3.70 (s, 3H), 3.41-2.90 (m, 2H+1H+OH).

Preparation of Compound 6

(S)-2-((S)-2-((S)-hydroxy-(5-(4-methoxybenzyloxy)-1-phenyl-1H-pyrazol-3-yl)methyl)but-3-enamido)succinic acid

6

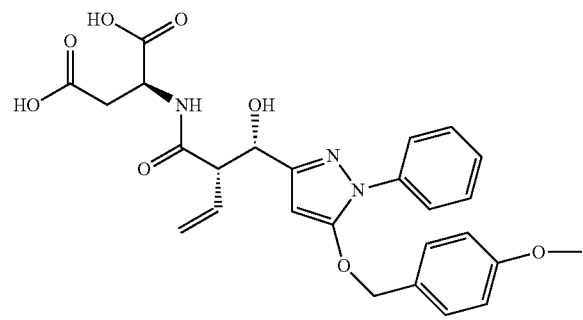

Compound 6 corresponds to formula (I) in which:
$R_1$ has the same meaning as for compound 4,
$R_2$=—(CH$_2$)$_n$—R$_{12}$, with n=1 and R$_{12}$=COOH,
$R_3$ has the same meaning as for compound 3.

Stage A

Preparation of (S)-dimethyl 2-acrylamidosuccinate 22 mmol of triethylamine and then 10 mmol of acryloyl chloride are added, at 0° C., under an inert atmosphere, to a solution of 10 mmol of H-aspartic dimethyl ester hydrochloride in 20 ml of THF. After stirring for 1 hour at ambient temperature, the reaction mixture is hydrolyzed, and then extracted with ethyl acetate (3 times) and with dichloromethane (twice). The organic phases are dried over sodium sulfate, filtered, and concentrated under reduced pressure. Silica gel chromatography (cyclohexane/EtOAc: 7/3) makes it possible to isolate the expected product.

Stage B

Preparation of (S,E)-dimethyl 2-(4-(trimethylsilyl)but-2-enamido)succinate 7.5 mmol of allyltrimethylsilane and 0.1 mmol of the catalyst 1,3-bis(2,4,6-trimethylphenyl)-2-imidazolidinylidene)dichloro(o-isopropoxyphenylmethylene)-ruthenium are added to a solution of 2.5 mmol of the compound obtained in stage A in 15 ml of dichloromethane. After stirring for 36 hours at ambient temperature, the solution is evaporated under vacuum. Silica gel chromatography (cyclohexane/EtOAc: 7/3) makes it possible to isolate the expected product.

Stage C

Preparation of (S)-dimethyl 2-((S)-2-((S)-hydroxy-(5-(4-methoxybenzyloxy)-1-phenyl-1H-pyrazol-3-yl)methyl)but-3-enamido)succinate 1 mmol of 5-(4-methoxybenzyloxy)-1-phenyl-1H-pyrazole-3-carbaldehyde and then 1.1 ml of tetrabutylammonium fluoride are added successively, at −78° C., to a solution of 1 mmol of the compound obtained in stage B in 5 ml of THF or acetone. After stirring for 15 minutes at this temperature, the reaction mixture is hydrolyzed with a saturated ammonium chloride solution, and then extracted with ethyl acetate (3 times). The organic phases are dried over sodium sulfate, filtered, and concentrated under reduced pressure. Silica gel chromatography (dichloromethane/methanol: 99/1) makes it possible to isolate the expected product in solid form.

Stage D

Preparation of (S)-2-((S)-2-((S)-hydroxy-(5-(4-methoxybenzyloxy)-1-phenyl-1H-pyrazol-3-yl)methyl)but-3-enamido)succinic acid (6)

2 mmol of LiOH are added to 0.5 mmol of the compound obtained in stage C in a 3/1: THF/H$_2$O mixture. After stirring for 3 hours at 25° C., the solvents are evaporated off, and the residual aqueous phase is diluted with water, acidified to pH=2 by adding a 5% hydrochloric acid solution, and then extracted with ethyl acetate. The combined organic phases are washed, dried, filtered, and then evaporated under reduced pressure. Silica gel chromatography (dichloromethane/methanol: 92/8) makes it possible to isolate the expected product 6 in solid form. HRMS calculated: 508.1720 [(M−H$^+$), C$_{26}$H$_{26}$N$_3$O$_8$]. found: 508.1717. $^1$H NMR (DMSO, 300 MHz) δ: 7.61-6.95 (1 m, 14H+NH), 5.95 (m, 1H), 5.75 (m, 1H pyrazole), 5.29-5.0 (1 m, 2H+NH), 5.12 (s, 2H OCH2), 4.92 (m, 1H), 4.69 (m, 1H), 3.74 (s, 3H), 3.35-2.90 (m, 2H+1H).

Preparation of Compound 7

(S)-2-((2S,3R)-3-hydroxy-2-vinylheptanamido)-4-(methylthio)butanoic acid

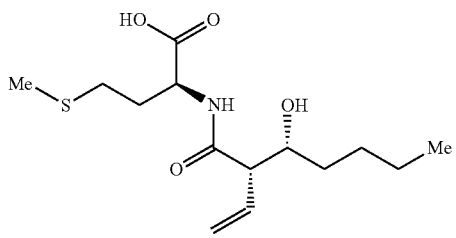

7

Compound 7 corresponds to formula (I) in which:
R$_1$ has the same meaning as for compound 4,
R$_2$=—(CH$_2$)$_n$—R$_{12}$, with n=2 and R$_{12}$=SR$_9$ with R$_9$=alkyl, namely methyl,
R$_3$=alkyl radical, namely butyl.

Stage A

Preparation of (S)-methyl 2-acrylamido-4-(methylthio)butanoate 22 mmol of triethylamine and then 10 mmol of acryloyl chloride are added, at 0° C., under an inert atmosphere, to a solution of 10 mmol of H-methionine methyl ester hydrochloride in 20 ml of THF. After stirring for 1 hour at ambient temperature, the reaction mixture is hydrolyzed and then extracted with ethyl acetate (3 times) and with dichloromethane (twice). The organic phases are dried over sodium sulfate, filtered, and concentrated under reduced pressure. Silica gel chromatography (cyclohexane/EtOAc: 7/3) makes it possible to isolate the expected product in the form of a white solid.

Stage B

Preparation of (S,E)-methyl 4-(methylthio)-2-(4-(trimethylsilyl)but-2-enamido)butanoate 9 mmol of allyltrimethylsilane and 0.09 mmol of the catalyst 1,3-bis(2,4,6-trimethylphenyl)-2-imidazolidinylidene)dichloro(o-isopropoxyphenylmethylene)-ruthenium are added to a solution of 3 mmol of the compound obtained in stage A in 15 ml of dichloromethane. After stirring for 36 hours at ambient temperature, the solution is evaporated under vacuum. Silica gel chromatography (cyclohexane/EtOAc: 7/3) makes it possible to isolate the expected product.

Stage C

Preparation of (S)-methyl-2-((2S,3R)-3-hydroxy-2-vinylheptanamido)-4-(methylthio)butanoate 1.1 mmol of pentanal and then 1.1 ml of tetrabutylammonium fluoride are added successively, at −78° C., to a solution of 1 mmol of the compound obtained in stage B in 5 ml of THF or acetone. After stirring for 15 minutes at this same temperature, the reaction mixture is hydrolyzed with a saturated ammonium chloride solution, and then extracted with ethyl acetate (3 times). The organic phases are dried over sodium sulfate, filtered, and concentrated under reduced pressure. Silica gel chromatography (dichloromethane/methanol: 99/1) makes it possible to isolate the expected product in solid form.

Stage D

Preparation of (S)-2-((2S,3R)-3-hydroxy-2-vinyl-heptanamido)-4-(methylthio)-butanoic acid (7)

1 mmol of LiOH is added to 0.5 mmol of the compound obtained in stage C in a 3/1: THF/H$_2$O mixture. After stirring for 3 hours at 25° C., the solvents are evaporated off, and the residual aqueous phase is diluted with water, acidified to pH=2 by adding a 5% hydrochloric acid solution, and then extracted with ethyl acetate. The combined organic phases are washed, dried, filtered, and then evaporated under reduced pressure. Silica gel chromatography (dichloromethane/methanol: 92/8) makes it possible to isolate the expected product 7 in solid form. HRMS calculated: 302.1426 [(M−H$^+$), C$_{14}$H$_{24}$NO$_4$S]. found: 302.1419. $^1$H NMR (CDCl$_3$, 300 MHz) δ: 6.84 (d, J=9 Hz, 1H, NH), 6.25 (bs, OH), 5.92 (m, 1H), 5.32 (d, J=10.9 Hz, 1H), 5.24 (d, J=14.7 Hz, 1H), 4.62 (m, 1H), 4.05 (m, 1H), 2.96 (m, 1H), 2.48 (m, 2H), 2.51-1.75 (m, 2H), 2.04 (s, 3H), 1.49-1.10 (m, 6H), 0.82 (t, J=6.7 Hz, 3H).

EXAMPLE 2

Process for Preparing a Compound 8 Corresponding to General Formula (I) in which Y Represents an Oxygen Atom and R$_4$ a Doublet of Electrons Preparation of (S)-((1S,2R,5S)-2-isopropyl-5-methylcyclohexyl)-2-((R)-1-hydroxyethyl)but-3-enoate (8)

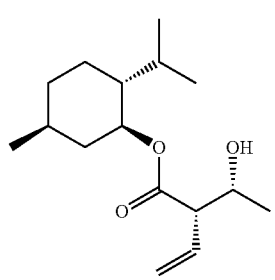

8

Compound 8 corresponds to formula (I) in which:
Y represents oxygen and $R_4$ a doublet of electrons,
$R_1$ and $R_2$ together form a cycloalkyl radical substituted with 2 alkyls, namely 2-isopropyl-5-methylcyclohexyl,
$R_3$ represents an alkyl radical, namely methyl,
$R_5$ represents an $XR_6R_7$ radical in which X represents an oxygen atom, $R_6$ represents a hydrogen and $R_7$ represents a doublet of electrons.

Stage A

Preparation of (1S,2R,5S)-2-isopropyl-5-methylcyclohexyl acrylate 22 mmol of diisopropylmethylamine and then 10 mmol of acryloyl chloride are added, at −78° C., under an inert atmosphere, to a solution of 10 mmol of (1R,2S,5R)-(−)-menthol in 20 ml of $CH_2Cl_2$ (dichloromethane). After stirring for 1 hour at ambient temperature, the reaction mixture is hydrolyzed, and then extracted with ethyl acetate (3 times) and with dichloromethane (twice). The organic phases are dried over sodium sulfate, filtered, and concentrated under reduced pressure. Silica gel chromatography (cyclohexane/EtOAc: 9/1) makes it possible to isolate the expected product in the form of a white solid.

Stage B

Preparation of (E)-((1S,2R,5S)-2-isopropyl-5-methylcyclohexyl)-4-(trimethyl-silyl)but-2-enoate 6 mmol of allyltrimethylsilane and 0.08 mmol of the catalyst 1,3-bis(2,4,6-trimethylphenyl)-2-imidazolidinylidene)dichloro(o-isopropoxyphenylmethylene)-ruthenium are added to a solution of 2 mmol of the compound obtained in stage A in 15 ml of dichloromethane. After stirring for 24 hours at ambient temperature, the solution is evaporated under vacuum. Silica gel chromatography (cyclohexane/EtOAc: 9.5/0.5) makes it possible to isolate the expected product.

Stage C

Preparation of (S)-((1S,2R,5S)-2-isopropyl-5-methylcyclohexyl)-2-((R)-1-hydroxyethyl)but-3-enoate (8)

1.1 mmol of acetaldehyde and then 1.1 ml of tetrabutylammonium fluoride are added successively, at −78° C., to a solution of 1 mmol of the compound obtained in stage B in 5 ml of THF or acetone. After stirring for 15 minutes at this same temperature, the reaction mixture is hydrolyzed with a saturated ammonium chloride solution, and then extracted with ethyl acetate (3 times). The organic phases are dried over sodium sulfate, filtered, and concentrated under reduced pressure. Silica gel chromatography (cyclohexane/ethyl acetate: 8/2) makes it possible to isolate the expected product 8. $^1$H NMR (CDCl$_3$, 300 MHz) δ: 5.87 (m, 1H, CH=), 5.17 (m, 2H), 5.24 (d, J=14.7 Hz, 1H), 4.64 (m, 1H), 4.01 (m, 1H), 3.28 (m, 1H OH), 2.94 (m, 1H), 1.95-0.63 (unresolved peak, 20H).

EXAMPLE 3

Tests for Enzymatic Inhibition of Metalloproteases MMP-9 and MMP-12

The inhibition selectivity of the synthesized compounds 1 to 7 was tested with respect to MMP-9 and MMP-12.

The duality between the hydrophobic part ($S'_1$ pocket) and the hydrophilic part (zinc atom) of an MMP inhibitor plays an important role with regard to the degree of inhibition and consequently can also play a determining role in the inhibition selectivity with respect to a single MMP.

The inventors in particular studied the interactions between the hydrophobic part which occupies the $S'_1$ pocket of the MPP inhibitor with the compounds of the invention. More particularly, the various possible orientations and the various possibilities of introduction of the hydrophobic group, in particular for the $R_1$ group of the compounds of the invention, were studied.

Protocols of the Tests for Enzymatic Inhibition of MMP-9 and MMP-12

The enzymatic tests for screening compounds 1 to 7 were carried out in solution on two purified human enzymes: the gelatinase MMP-9 (Anaspec, USA) and the metalloelastase MMP-12 (Anaspec, USA).

The activity is revealed by means of a colorimetric method suitable for a 96-well plate format.

The principle is based on the cleavage, by the MMP-9 or MMP-12 enzyme, of a chromogenic substrate: the thiopeptide (Ac-Pro-Leu-Gly-[2-mercapto-4-methylpentanoyl]-Leu-Gly-OC$_2$H$_5$) (Enzo Life Sciences, USA).

The hydrolysis of this thiopeptide produces a sulfhydryl group which reacts with Ellman's reagent: 5,5'-dithiobis(2-nitrobenzoic acid) (DTNB) to form 2-nitro-5-thiobenzoic acid (TNB), which is detected by its absorbance at 412 nm The tests are carried out in the buffer 50 mM Hepes, 10 mM CaCl$_2$, 0.5% Brij35, 1 mM DTNB, pH 7.0 containing the purified MMP-9 and MMP-12 enzymes diluted to the final concentration of 0.8 μg/ml.

After preincubation of the enzymes (1 h at ambient temperature in the dark) with or without the products tested (minimum of four doses serially diluted one-in-ten), the cleavage reactions are initiated by adding 150 μM (final concentration) of substrate in a total final volume of 100 μl (96-well plate format).

The plates containing the reactions are read in a microplate reader (Multiskan Ascent, ThermoElectron, France) in order to continuously measure the absorbance and to record values every 3 mM for 3 h. Each condition is carried out in triplicate.

The concentration which inhibits 50% of the reaction (IC$_{50}$) is determined from curves representing the absorbance (optical density) of the final reaction product (TNB) as a function of the doses tested. Each experiment is carried out at least twice.

Results

During this test, compounds 1 to 7 of the invention exhibited IC$_{50}$ values of between 5 and 330 μM and K$_i$ (inhibition constant) values of between 2.5 and 160 μM for the MMP-9 and MMP-12 enzymes (see table 1 below).

TABLE 1

| Inhibitor | IC50 MMP9 (μM) | K$_i$ MMP9 (μM) | IC50 MMP12 (μM) | K$_i$ MMP12 (μM) |
|---|---|---|---|---|
| 1 | 18.10 | 8.95 | 19.54 | 9.95 |
| 2 | 125.9 | 62.23 | 19.98 | 10.17 |
| 3 | 5 | 2.47 | 7.23 | 3.68 |
| 4 | 259.3 | 128.17 | 20.18 | 10.27 |
| 5 | 19.79 | 9.78 | 22.31 | 11.36 |
| 6 | 13.09 | 6.47 | 6.30 | 3.21 |
| 7 | 330.4 | 163.32 | 78.33 | 39.87 |

Analysis of the Results and Conclusion

According to biological tests results table 1, the 7 compounds tested can be divided up into two categories, namely, on the one hand, compounds 1, 3 and 5, and, on the other hand, compounds 2, 4, 6 and 7.

The first category (compounds 1, 3, and 5) corresponds to the compounds which have similar inhibition values on the two MMPs tested.

Compounds 1 and 3 have binding modes which are very original and different with respect to MMP-12 and MMP-9. Compound 5, for its part, has the same binding mode with respect to the two MMPs.

More particularly, compound 1 is very advantageous by virtue of its low number of atoms and its good biological activity. It has an identical $K_i$ with respect to the two enzymes MMP-12 and MMP-9, but its binding mode is very different with these two enzymes.

Figure 3:
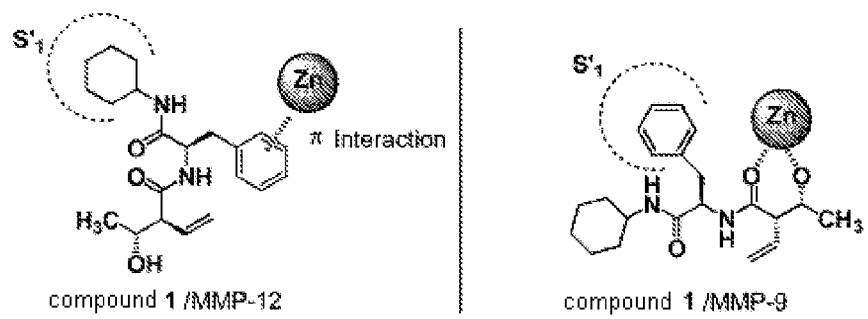
FIG. 3 illustrates, respectively, the interactions of compound 1 of the invention with the MMP-12 inhibitor (figure on the left) and with the MMP-9 inhibitor (figure on the right).

Compound 1 behaves with respect to MMP-9 like a pseudopeptide inhibitor with the formation of two hydrogen bonds with the backbones of the residues of the groove of the protein substrate. The benzyl part of compound 1 (namely the substituent $R_2$) interacts with the hydrophobic pocket $S'_1$ of MMP-9 and the carbonyl of the hydroxy acid part of compound 1 chelates the zinc atom of MMP-9 (see FIG. 3, right).

When it interacts with MMP-12, the cyclohexylcarboxamide part (namely the substituent $R_1$) of compound 1 is in the $S'_1$ pocket of MMP-12 and the hydroxy acid part interacts with the groove of the protein substrate by forming two hydrogen bonds. The interaction with the zinc atom takes place by means of the benzyl radical (substituent $R_2$) of compound 1 by forming π-cation interactions (see FIG. 3, left). This interaction is entirely original in the inhibition of matrix metalloproteinases.

Compound 3 also has the same $K_i$ value with respect to the two enzymes. However, two binding modes are demonstrated with respect to MMP-12 and MMP-9.

With the structure of MMP-9, the formation of a zinc-chelating pincer is noted between the carbonyl and the hydroxyl function of the central part of compound 3. The pyrazole part (substituent $R_3$) of compound 3 interacts with the $S'_1$ pocket by means of its phenyl radical (FIG. 4, right).

Figure 4:
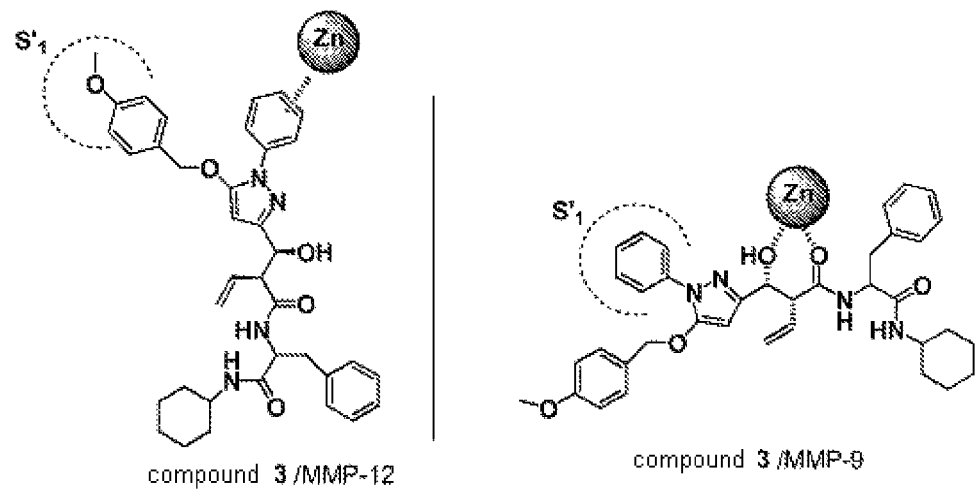
FIG. 4 illustrates, respectively, the interactions of compound 3 of the invention with the MMP-12 inhibitor (figure on the left) and with the MMP-9 inhibitor (figure on the right).

With MMP-12, the pyrazole part of compound 3 interacts with the $S'_1$ pocket via its p-methoxybenzyloxy radical and forms once again a π-cation interaction with its phenyl radical and the zinc atom (FIG. 4, left).

Compound 3 is itself also very advantageous by virtue of its particular binding mode wherein the pyrazole part interacts with the $S'_1$ pocket and forms once again a π-cation interaction with the zinc atom. The chirality of the amino acid part does not appear to be important for the activity.

The second category of compounds (compounds 2, 4, 6 and 7) exhibits different inhibition values on the two MMPs, with an increasing factor of 2 to 13 times in favor of MMP-12. Compound 2 is found to be particularly advantageous.

Figure 5:
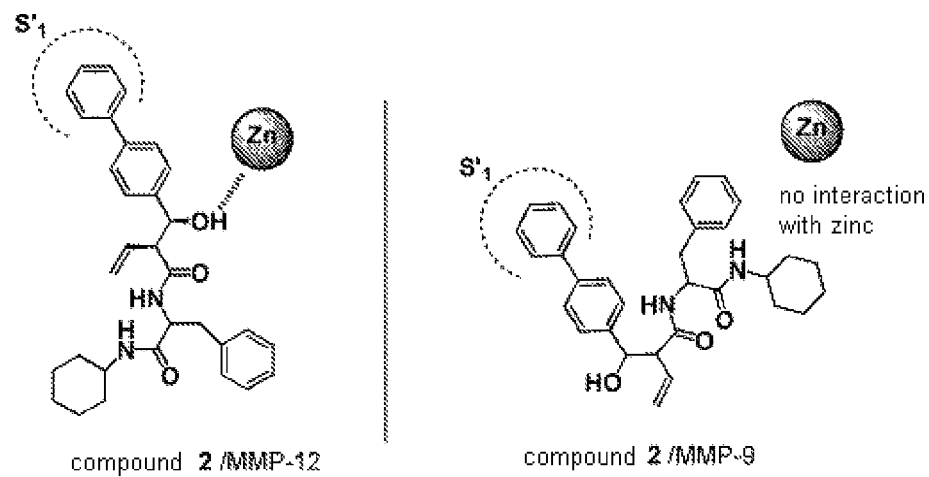
FIG. 5 illustrates, respectively, the interactions of compound 2 of the invention with the MMP-12 inhibitor (figure on the left) and with the MMP-9 inhibitor (figure on the right).
Figure 6:
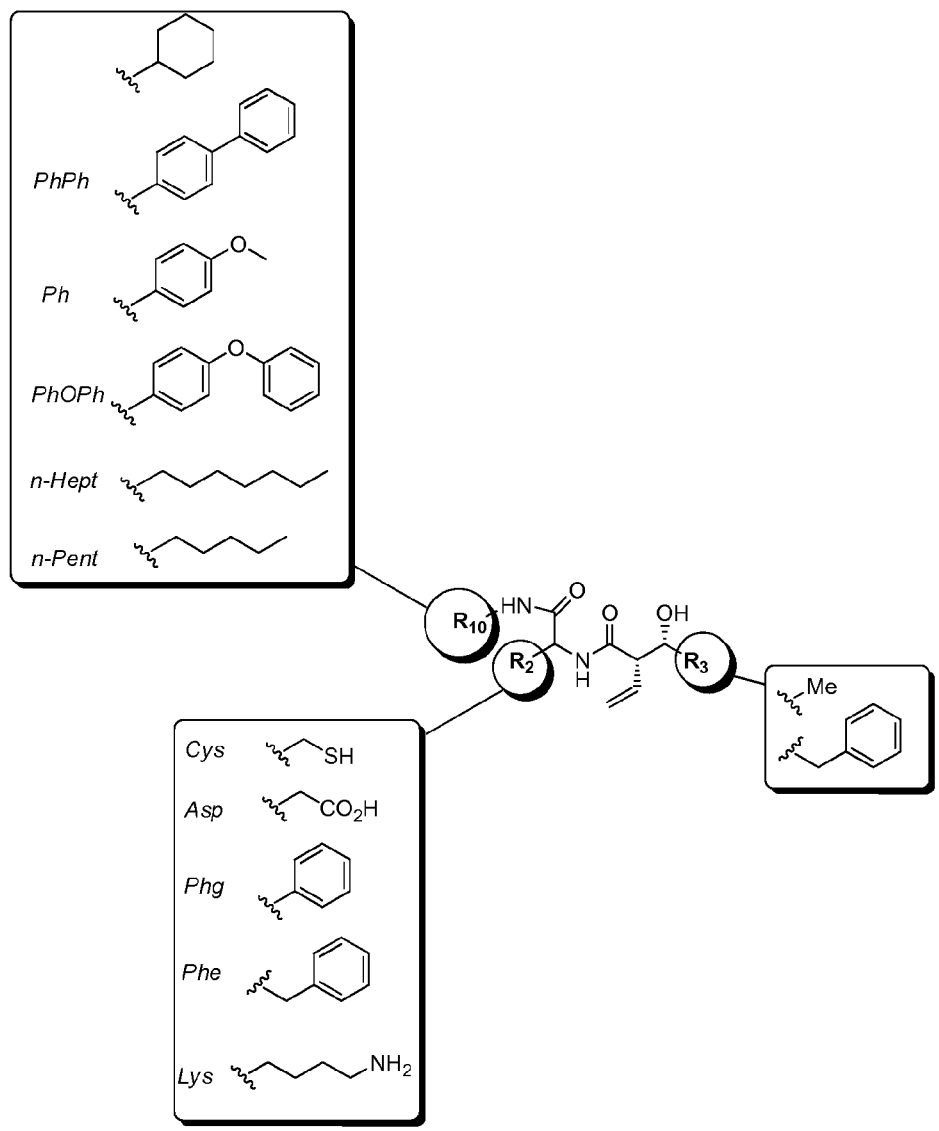
FIG. 6 relates to specific examples of compounds of the invention corresponding to formula (I).

This is because a difference in $K_i$ by a factor of 6 is demonstrated with compound 2. However, this compound exhibits the same binding mode characterized by an interaction with the $S'_1$ pocket by means of its biphenyl part (substituent $R_3$). The benzyl part of compound 2 mimics the protein substrate in its groove by forming three hydrogen bonds for MMP-12 and only one hydrogen bond with MMP-9. It can be noted that the hydroxyl function of compound 2 chelates the zinc atom of MMP-12 (FIG. 5, left), whereas no interaction is observed with the zinc atom in the case of MMP-9 (FIG. 5, left), thereby certainly explaining this selectivity.

Compound 2 is therefore particularly promising and exhibits good selectivity with respect to MMP-12.

CONCLUSION

The compounds of the invention distinguish themselves for their biological activities (selectivity with respect to MMP-12 and/or MMP-9) and their binding modes. Indeed, they generate binding modes which are very original and selective according to the MMP targeted (π-cation interaction). The binding modes of the compounds of the invention with the MMP matrix metalloproteases are very different than those of the prior art compounds known to be MMP inhibitors, for instance Marimastat, which itself always binds with the zinc part of MMPs by means of its hydroxamic acid part, which is not the case with the compounds of the invention.

The compounds of the invention made it possible to define the duality between the hydrophobic ($S'_1$ pocket) and hydrophilic (zinc atom) binding mode of the MMP inhibitor.

Advantageously, the compounds of the invention are selective inhibitors of metalloproteases, and in particular of matrix metalloproteases 12 (MMP-12) and 9 (MMP-9), and even more particularly of MMP-12.

The compounds of the invention also prove to be advantageous because of their particularly advantageous production process: low number of steps (3-4) for synthesizing said compounds, "modulability" of the process at each step of the synthesis (diversity of structures for better inhibition selectivity).

EXAMPLE 4

Study of the Docking Score of Compounds Corresponding to Formula (I)

Various compounds corresponding to formula (I) below:

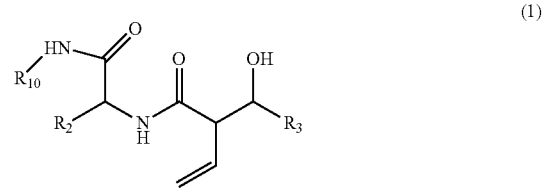

(1)

in which the substituent $R_1$ is represented by the —$CONHR_{10}$ radial, Y is represented by nitrogen, $R_4$ is represented by hydrogen and $R_5$ is represented by the hydroxyl OH, were tested in a study of the docking score, by varying the substituents $R_{10}$, $R_2$ and $R_3$ in the manner represented in table 2 below.

These compounds were denoted by the numbers 1 and 9 to 36.

The measurement of the docking score makes it possible to give a provisional value for the inhibition. The higher the value of the docking score in absolute value, the better the inhibition.

The values of certain pharmacokinetic parameters were also measured. These parameters, which are important for obtaining activity in vivo, can be predicted by virtue of the "QuickProp" module of the Schrodinger suite.

The "QplogPo/w" parameter corresponds to the water/octanol partition coefficient commonly referred to as "Log P". The optimal values of this parameter (Lipinzky's rule) are between 3 and 5 (<3 for nonpolar compounds targeting the central nervous system).

The "QplogHERG" parameter corresponds to the log of the $IC_{50}$ of the compound studied with respect to very important potassium-ion cardiac channels. Thus, if this value is less than −5, the compound can induce cardiac toxicity.

TABLE 2

| Compo (I) | $R_3$ | $R_2$ | $R_{10}$ | docking score | QPlogPo/w | QPlogHERG |
|---|---|---|---|---|---|---|
| 9 | Me | $CH_2CO_2H$ | $C_6H_4OC_6H_5$ | −15.316476 | 3.513 | −3.345 |
| 10 | $CH_2C_6H_5$ | $CH_2CO_2H$ | $C_6H_4OC_6H_5$ | −6.992449 | 3.154 | −3.061 |
| 1 | Me | $CH_2C_6H_5$ | $C_6H_{11}$ | −7.427621 | 3.416 | −2.801 |
| 11 | $CH_2C_6H_5$ | $CH_2C_6H_5$ | $C_6H_{11}$ | −7.450145 | 3.393 | −2.988 |
| 12 | Me | $CH_2C_6H_5$ | $n\text{-}C_7H_{15}$ | −7.243734 | 3.984 | −2.873 |
| 13 | Me | $CH_2C_6H_5$ | $n\text{-}C_5H_{11}$ | −7.164123 | 3.525 | −3.328 |
| 14 | Me | $CH_2C_6H_5$ | $C_6H_4OMe$ | −8.57941 | 3.928 | −5.064 |
| 15 | Me | $CH_2C_6H_5$ | $C_6H_4OC_6H_5$ | −8.981474 | 5.29 | −6.054 |
| 16 | Me | $CH_2C_6H_5$ | $C_6H_4C_6H_5$ | −8.944325 | 5.581 | −6.061 |
| 17 | Me | $CH_2SH$ | $C_6H_{11}$ | −10.492747 | 2.802 | −2.085 |
| 18 | $CH_2C_6H_5$ | $CH_2SH$ | $C_6H_{11}$ | −7.181084 | 2.666 | −1.734 |
| 19 | Me | $CH_2S^-$ | $C_6H_4OC_6H_5$ | −12.917503 | 4.746 | −5.205 |
| 20 | Me | $CH_2SH$ | $C_6H_4OC_6H_5$ | −9.85305 | 4.395 | −4.794 |
| 21 | $CH_2C_6H_5$ | $CH_2S^-$ | $C_6H_4OC_6H_5$ | −13.196498 | 6.539 | −6.657 |
| 22 | $CH_2C_6H_5$ | $CH_2SH$ | $C_6H_4OC_6H_5$ | −10.695544 | 6.405 | −6.531 |
| 23 | Me | $CH_2CO_2H$ | $C_6H_4OC_6H_5$ | −13.871861 | 3.486 | −3.306 |
| 24 | Me | $CH_2C_6H_5$ | $C_6H_{11}$ | −7.568168 | 3.524 | −3.086 |
| 25 | Me | $CH_2SH$ | $C_6H_{11}$ | −11.109145 | 2.665 | −1.847 |
| 26 | $CH_2C_6H_5$ | $CH_2SH$ | $C_6H_{11}$ | −6.530526 | 2.605 | −1.555 |
| 27 | Me | $CH_2S^-$ | $C_6H_4OC_6H_5$ | −12.82189 | 4.623 | −5.075 |
| 28 | Me | $CH_2SH$ | $C_6H_4OC_6H_5$ | −9.953112 | 4.623 | −5.237 |
| 29 | $CH_2C_6H_5$ | $CH_2S^-$ | $C_6H_4OC_6H_5$ | −12.957148 | 6.031 | −5.598 |
| 30 | $CH_2C_6H_5$ | $CH_2SH$ | $C_6H_4OC_6H_5$ | −9.821999 | 6.433 | −6.576 |
| 31 | Me | $C_4H_8NH_2$ | $C_6H_{11}$ | −6.505873 | 1.3 | −2.821 |
| 32 | Me | $C_6H_5$ | $C_6H_{11}$ | −7.825161 | 3.214 | −2.591 |
| 33 | Me | $CH_2C_6H_4OH$ | $C_6H_{11}$ | −7.855433 | 2.626 | −2.563 |
| 34 | Me | $C_4H_8NH_2$ | $C_6H_{11}$ | −7.034941 | 1.115 | −2.688 |
| 35 | Me | $C_6H_5$ | $C_6H_{11}$ | −7.160804 | 3.03 | −2.64 |
| 36 | Me | $CH_2C_6H_4OH$ | $C_6H_{11}$ | −7.909279 | 2.793 | −2.837 |

By way of indication, the chirality of the amino acid part is "D" for compounds 24 to 33 described above.

Compounds 9, 15, 17 and 20, represented respectively by the chemical formulae and names below, have in particular advantageous docking score values:

(S)-3-((S)-2-((R)-1-hydroxyethyl)but-3-enamido)-4-oxo-4-(4-phenoxy-phenylamino)butanoic acid

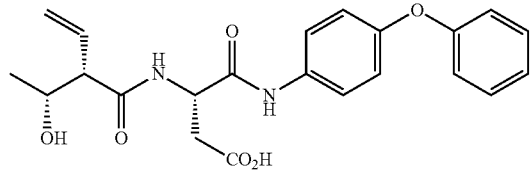 [SMILES: C=C[C@H](C(=O)N[C@@H](CC(=O)O)C(=O)Nc1ccc(Oc2ccccc2)cc1)[C@@H](C)O]

(S)-2-((R)-1-hydroxyethyl)-N—((S)-1-oxo-1-(4-phenoxy-phenylamino)-3-phenylpropan-2-yl)but-3-enamide

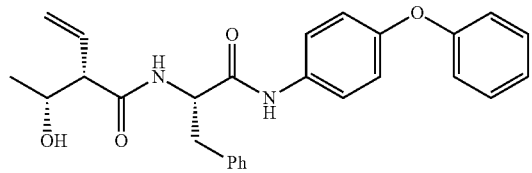 [SMILES: C=C[C@H](C(=O)N[C@@H](Cc1ccccc1)C(=O)Nc1ccc(Oc2ccccc2)cc1)[C@@H](C)O]

(S)—N—((R)-1-(cyclohexylamino)-3-mercapto-1-oxopropan-2-yl)-2-((R)-1-hydroxyethyl)but-3-enamide

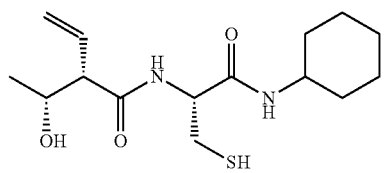 [SMILES: C=C[C@H](C(=O)N[C@@H](CS)C(=O)NC1CCCCC1)[C@@H](C)O]

(S)-2-((R)-1-hydroxyethyl)-N—((R)-3-mercapto-1-oxo-1-(4-phenoxyphenyl-amino)propan-2-yl)but-3-enamide

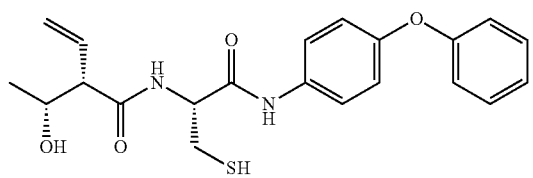 [SMILES: C=C[C@H](C(=O)N[C@@H](CS)C(=O)Nc1ccc(Oc2ccccc2)cc1)[C@@H](C)O]

However, other compounds of table 2 also have advantageous docking score values.

The pharmacokinetic parameters important for in vivo activity were modeled by virtue of the QuickProp module of the Schrodinger suite. The parameters of some of the compounds of the invention tested are in agreement with a future evaluation in vivo; an oral absorption greater than 90% with an optimal intestine-blood passive transport and a very weak interaction with the Herg potassium channels responsible for cardiac toxicity, torsade de pointes, QT interval prolongation, etc.

LITERATURE REFERENCES (1) Sternlicht M. D et al., *Annu Rev Cell Dev Biol*, 2001, 17.
(2) Hautamaki R D et al., *Science* 1997, 277 2002-4.
(3) Luisetti M et al., *Eur Respir J.* 1996, 9, 1482.
(4) Hashimoto N et al., *Jpn J Antibiot.* 2001, 54, 137.
(5) Kanai K et al, *Mediators Inflamm.* 2004, 13, 313.
(6) Overall, C. M. et al., O. *Nat. Rev. Cancer* 2006, 6, 227-239.
(7) Whittaker, M. et al., *Chem. Rev,* 1999, 99, 2735-2776.
(8) Hanemaaijer R et al., *Adv Dent Res.* 1998, 12, 114.
(9) Churg A et al., *Am J Respir Cell Mol Biol.* 2002, 27, 368.
(10) Pemberton P A et al. *COPD.* 2005, 2, 303.
(11) Hidalgo M et al., *J. Natl Cancer Inst* 2001, 93: 178-93.
(12) Brown P D. APMIS (*Copenhagen*) 1999, 107, 174-80.
(13) Rudek M A et al. *J Clin Oncol* 2001, 19, 584-92.
(14) Bremer C et al., *Nat Med* 2001, 7, 743-8.

The invention claimed is:

1. An α-vinyl carbonyl compound characterized in that it has formula (I):

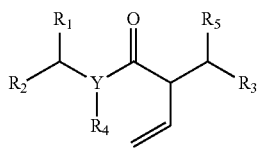

in which
$R_1$ represents an acyl radical of formula —CO—$R_8$, in which $R_8$ represents OH, NHR$_{10}$ or NR$_{10}$R$_{11}$, with $R_{10}$ and $R_{11}$, which may be identical or different, representing, independently of one another, hydrogen, alkyl, alkenyl, alkynyl, OH, phenyl ($C_6H_5$), methoxyphenyl ($C_6H_4OCH_3$), phenyloxyphenyl ($C_6H_4OC_6H_5$), biphenyl ($C_{12}H_9$), benzyl ($CH_2C_6H_5$), cyclohexyl ($C_6H_{11}$), cyclopentyl ($C_5H_9$), $R_2$ or $R_3$, which may be identical or different, represent, independently of one another:
an alkyl, alkenyl, alkynyl radical,
a —$(CH_2)_n$—$R_{12}$ radical, in which n represents an integer ranging from 1 to 6, with $R_{12}$ representing OH, phenyl, biphenyl, benzyl, cyclohexyl, cyclopentyl, COOH, COOR$_9$, SR$_9$, S$^-$(cation), with $R_9$ representing hydrogen, alkyl, alkenyl, alkynyl,
a —$(CH_2)_n$—N—$(R_9)_2$ or —$(CH_2)_n$—N—$(COO$—$R_9)_2$ radical in which n represents an integer ranging from 1 to 6,
a cycloalkyl radical,
an aryl radical, or
$R_1$ and $R_2$ together form a cycloalkyl or aryl radical,
Y represents a nitrogen or oxygen atom,
$R_4$ represents a hydrogen atom, an alkyl, alkenyl, alkynyl or aryl radical, a doublet of electrons, a —$(CH_2)_n$-$R_{12}$ radical with n and $R_{12}$ as previously defined,
$R_5$ represents:
an XR$_6$R$_7$ radical with X representing an oxygen, nitrogen or sulfur atom, R$_6$ and R$_7$, which may be identical or different, representing, independently of one another, a hydrogen atom, an alkyl radical, a doublet of electrons, an SO$_2$R$_{13}$ radical with R$_{13}$ representing an alkyl, alkenyl, alkynyl, aryl radical as previously defined, a —$(CH_2)_n$—$R_{12}$ radical as previously defined,
a halogen,
an alkyl, alkenyl, akynyl radical,
isomers thereof, diastereoisomers thereof and addition salts thereof with a pharmaceutically acceptable acid or base.

2. The compound as claimed in claim 1, characterized in that, in formula (I):
Y represents a nitrogen atom and $R_4$ represents a hydrogen atom,
$R_5$ represents an XR$_6$R$_7$ radical in which X represents an oxygen atom, $R_6$ represents a hydrogen and $R_7$ represents a doublet of electrons,
$R_1$ represents an acyl radical of formula —CO—$R_8$, in which $R_8$ represents OH or NHR$_{10}$ with $R_{10}$ as defined in claim 1.

3. The compound as claimed in claim 1, characterized in that, in formula (I), $R_2$ represents a —$(CH_2)_n$—$R_{12}$ radical, a —$(CH_2)_n$—N—$(R_9)_2$ radical or an aryl radical as defined in claim 1.

4. The compound as claimed in claim 1, characterized in that, in formula (I), $R_3$ represents an alkyl radical or an aryl radical as defined in claim 1.

5. The compound of formula (I) as claimed in claim 1, characterized in that it is selected from the group consisting of:
(S)-N-((S)-1-(cyclohexylamino)-1-oxo-3-phenylpropan-2-yl)-2-(R)-1-hydroxyethyl)but-3-enamide,
(S)-2-((S)-biphenyl-4-yl(hydroxyl)methyl)-N-((S)-1-(cyclohexylamino)-1-oxo-3-phenylpropan-2-yl)but-3-enamide,
(S)-N-((S)-1-(cyclohexylamino)-1-oxo-3-phenylpropan-2-yl)-2-((S)-hydroxy-(5-(4-methoxybenzyloxy)-1-phenyl-1H-pyrazol-3-yl)methyl)but-3-enamide,
(S)-2-((S)-2-((S)-hydroxy-5(4-methoxybenzyloxy)-1-phenyl-1H-pyrazol-3-yl)methyl)but-3-enamido)-3-phenylpropanoic acid,
(S)-2-((S)-hydroxy-(5-(4-methoxybenzyloxy)-1-phenyl-1H-pyrazol-3-yl)methyl-N-((S)-1-(hydroxyamino)-1-oxo-3-phenylpropan-2-yl)but-3-enamide,
(S)-2-((S)-2-((S)-hydroxy-(5-(4-methoxybenzyloxy)-1-phenyl-1H-pyrazol-3-yl)methyl)but-3-enamido)succinic acid,
(S)-2-((2S,3R)-3-hydroxy-2-vinylheptanamido)-4-(methylthio)butanoic acid,
(S)-2-((R)-1-hydroxyethyl)-N-((S)-1-oxo-1-(4-phenoxyphenylamino)-3-phenylpropan-2-yl)but-3-enamide,
(S)-3-((S)-2-((R)-1-hydroxyethyl)but-3-enamido)-4-oxo-4-(4-phenoxyphenylamino)butanoic acid,
(S)-2-((R)-1-hydroxyethyl)-N-((R)-3-mercapto-1-oxo-1-(4-phenoxyphenylamino)propan-2-yl)but-3-enamide,
(S)-N-((R)-1-(cyclohexylamino)-3-mercapto-1-oxopropan-2-yl)-2-((R)-1-hydroxyethyl)but-3-enamide,
and mixtures thereof.

6. The compound as claimed in claim 1, characterized in that, in formula (I):
Y represents an oxygen atom and $R_4$ represents a doublet of electrons,
$R_5$ represents an XR$_6$R$_7$ radical in which X represents an oxygen atom, $R_6$ represents a hydrogen and $R_7$ represents a doublet of electrons.

7. The compound as claimed in claim 6, characterized in that, in formula (I), $R_1$ and $R_2$ together form a cycloalkyl or aryl radical.

8. The compound of formula (I) as claimed in claim 1, which is (S)-((1S,2R,5S)-2-isopropyl-5-methylcyclohexyl)-2-((R)-1-hydroxyethyl)but-3-enoate.

9. A process for producing the compounds of formula (I) as claimed in claim 1, characterized in that it comprises the following steps:

reacting a compound of formula (II):

(II)

$$\underset{R_2}{\overset{R_1}{>}}\!\!\!\!-\!\!\underset{R_4}{NH}$$

in which $R_1$, $R_2$ and $R_4$ are as defined in formula (I), with a compound of formula (II'):

(II')

[acryloyl chloride structure]

so as to produce the compounds of formula (III), (III)

[R_1R_2CH-NR_4-C(O)-CH=CH_2 structure]

in which $R_1$, $R_2$ and $R_4$ are as previously defined, Y representing a nitrogen atom, reacting the compound (III) obtained in the previous step, under neutral conditions, with a compound of formula (III'):

(III')

[allyltrimethylsilane structure, CH_2=CH-CH_2-SiMe_3]

so as to produce the compounds of formula (IV):

(IV)

[R_1R_2CH-NR_4-C(O)-CH=CH-CH_2-SiMe_3 structure]

in which $R_1$, $R_2$, $R_4$ and Y are as previously defined, reacting the compound of formula (IV) obtained in the previous step, under basic conditions, with a compound of formula (IV'):

$R_3$CHO  (IV')

in which $R_3$ is as defined in formula (I)

so as to produce the compounds of formula (I):

(I)

[structure of formula I with R_1, R_2, Y, R_4, vinyl, and CH(OH)R_3 groups]

in which $R_1$, $R_2$, $R_3$ and $R_4$ are as defined in formula (I), Y represents a nitrogen.

10. A process for producing a compound of formula (I) as claimed in claim 1, characterized in that it comprises the following steps:

reacting a compound of formula (V):

(V)

$$\underset{R_2}{\overset{R_1}{>}}\!\!\!\!-\!\!OH$$

in which $R_1$ and $R_2$ are as defined in formula (I), with a compound of formula (II'):

(II')

[acryloyl chloride structure]

so as to produce the compounds of formula (VI):

(VI)

[R_1R_2CH-O-C(O)-CH=CH_2 structure]

in which $R_1$ and $R_2$ are as previously defined, reacting the compound (VI) obtained in the previous step, under neutral conditions, with a compound of formula (III'):

(III')

[allyltrimethylsilane structure]

so as to produce the compounds of formula (VII):

(VII)

[R_1R_2CH-O-C(O)-CH=CH-CH_2-SiMe_3 structure]

in which $R_1$ and $R_2$ are as previously defined, reacting the compound of formula (VII) obtained in the previous step, under basic conditions, with a compound of formula (IV'):

R₃CHO (IV')

in which R₃ is as defined in formula (I),
so as to produce the compounds of formula (I):

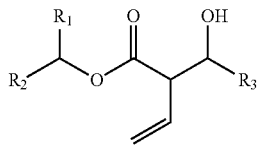
(I)

in which R₁, R₂ and R₃ are as defined in formula (I).

11. A method for treating or reducing the symptoms of chronic obstructive pulmonary disease (COPD) comprising administering to a subject in need thereof a compound of formula (I) as claimed in claim 1.

12. A composition comprising at least one compound of formula (I) as claimed in claim 1 and optionally at least one pharmaceutically acceptable excipient.

13. The method of claim 11, wherein said COPD comprises emphysema caused by cigarette smoke.

14. A method for treating or reducing the symptoms of chronic obstructive pulmonary disease (COPD) comprising administering to a subject in need thereof a compound of formula (I) as claimed in claim 5.

15. A method for treating or reducing the symptoms of chronic obstructive pulmonary disease (COPD) comprising administering to a subject in need thereof a compound of formula (I) as defined in claim 8.

16. The compound of formula (I) as claimed in claim 1, wherein :
   the cycloalkyl is selected from the group consisting of cyclopropyl, cyclobutyl, cyclopentyl, cyclohexyl or 2-isopropyl-5-methylcyclohexyl, and
   the aryl is selected from the group consisting of phenyl (C6H5), methoxyphenyl (C6H4OCH3), phenyloxyphenyl (C6H4OC6H5), benzyl (C6H5CH2), phenethyl (C6H5CH2CH2), tolyl (C6H4CH3), xylyl (C6H3(CH3)2), benzylidene (C6H5CH), benzoyl (C6H5CO), biphenyl (or diphenyl) (C12H9), naphthyl (C10H7), pyrazole or 5-(4-methoxybenzyloxy)-1-phenylpyrazole.

* * * * *